(12) United States Patent
De Bruijn

(10) Patent No.: US 11,655,485 B2
(45) Date of Patent: *May 23, 2023

(54) PROCESS FOR THE PRODUCTION OF ETHANOL

(71) Applicant: DSM IP ASSETS B.V., Heerlen (NL)

(72) Inventor: Hans Marinus Charles Johannes De Bruijn, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 0 days.

This patent is subject to a terminal disclaimer.

(21) Appl. No.: 17/271,034

(22) PCT Filed: Aug. 15, 2019

(86) PCT No.: PCT/EP2019/071901
§ 371 (c)(1),
(2) Date: Feb. 24, 2021

(87) PCT Pub. No.: WO2020/043497
PCT Pub. Date: Mar. 5, 2020

(65) Prior Publication Data
US 2021/0189438 A1    Jun. 24, 2021

(30) Foreign Application Priority Data

Aug. 28, 2018  (EP) ..................... 18191183

(51) Int. Cl.
C12P 7/06 (2006.01)
C12P 7/14 (2006.01)

(52) U.S. Cl.
CPC .. C12P 7/14 (2013.01); C12P 7/06 (2013.01)

(58) Field of Classification Search
CPC ....................................................... C12P 7/06
See application file for complete search history.

(56) References Cited

U.S. PATENT DOCUMENTS

| | | | |
|---|---|---|---|
| 7,335,501 B1 * | 2/2008 | Pierrard ................... | C12N 9/16 435/254.6 |
| 2017/0306310 A1 * | 10/2017 | Fukuyama ............. | C12N 9/242 |
| 2020/0407733 A1 | 12/2020 | De Bruijn et al. | |

FOREIGN PATENT DOCUMENTS

WO  2017/112631 A1  6/2017
WO  2019/063543 A1  4/2019

OTHER PUBLICATIONS

Database UniParc [Online], "*Punctularia strigosozonata* (strain HHB-11173)(White-rot fungus)," XP002788950, Database accession No. UPI00044178D1.
Database UniParc [Online], "*Ceriporiopsis subvermispora* (strain B) (White rot fungus)", XP002788951,Database accession No. UPI0002B2C95B.
Petit, et al, "Engineering industrial *Saccharomyces cerevisiae* strains for ethanol production from starchy substrates and by-products," 33rd International Specialised Symposium on Yeasts: Exploring and engineering yeasts for industrial application, University College Cork, Ireland, Poster Abstract, (2017), page cover, 99, XP002788960.
Navarro, et al, "Fast solubilization of recalcitrant cellulosic biomass by the basidiomycete fungus *Laetisaria arvalis* involves successive secretion of oxidative and hydrolytic enzymes," Biotechnology for Biofuels, (2014), vol. 7: pp. 1-14.
Kameshwar, et al., "Comparative study of genome-wide plant biomass-degrading CAZymes in white rat, brown rot and soft rot fungi," Mycology, (2018), vol. 9, No. 2: 93-105.
Favaro, et al., "Exploring industrial and natural *Saccharomyces cerevisiae* strains for the bio-based economy from biomass: the case of bioethanol," Critical Reviews in Biotechnology, (2019), vol. 39, No. 6: 800-816.
PCT International Search Report for PCT/EP2019/071901, dated Sep. 16, 2019.

* cited by examiner

Primary Examiner — Maryam Monshipouri
(74) Attorney, Agent, or Firm — McBee, Moore & Vanik IP, LLC

(57) ABSTRACT

The invention relates to a process for the production of ethanol comprising fermenting a (optionally liquefied) corn slurry under anaerobic conditions in the presence of a recombinant yeast; and recovering the ethanol, wherein said recombinant yeast functionally expresses a heterologous nucleic acid sequence encoding a glucoamylase having an amino acid sequence according to SEQ ID NO: 1 or which glucoamylase is a functional homologue thereof having a sequence identity of at least 80%, or which glucoamylase is a functional homologue which is derived, by way of one or more amino acid substitutions, deletions or insertions, from the amino acid sequence of SEQ ID NO: 1, and wherein the process comprises dosing a glucoamylase at a concentration of 0.05 g/L or less.

15 Claims, No Drawings
Specification includes a Sequence Listing.

PROCESS FOR THE PRODUCTION OF ETHANOL

CROSS-REFERENCE TO RELATED APPLICATIONS

This application is the National Stage entry of International Application No. PCT/EP2019/071901, filed 15 Aug. 2019, which claims priority to European Patent Application No. 18191183.5, filed 28 Aug. 2018.

REFERENCE TO SEQUENCE LISTING SUBMITTED AS A COMPLIANT ASCII TEXT FILE (.txt)

Pursuant to the EFS-Web legal framework and 37 C.F.R. § 1.821-825 (see M.P.E.P. § 2442.03(a)), a Sequence Listing in the form of an ASCII-compliant text file (entitled "2919208-551000_Sequence_Listing_ST25.txt" created on 8 Feb. 2021, and 11,524 bytes in size) is submitted concurrently with the instant application, and the entire contents of the Sequence Listing are incorporated herein by reference.

BACKGROUND

Field

Field of the Invention

The invention relates to a process for the production of ethanol and optionally distillers dried grains with solubles (DDGS) and to the distillers dried grains with solubles so obtained.

Description of Related Art

Ethanol production from starch-containing material is well-known in the art. As a first step, starch is usually converted into dextrins using an amylase. The dextrins are subsequentially hydrolyzed into D-glucose using glucoamylase. The glucose is fermented into ethanol. Amylase and glucoamylase are conventionally added to the starch media.

For example, US2017/0306310 describes a process of producing a fermentation product, particularly ethanol, from starch-containing material comprising the steps of: (a) liquefying starch-containing material in the presence of an alpha amylase; (b) saccharifying the liquefied material; and (c) fermenting with a fermenting organism; wherein step (b) is carried out using at least a variant glucoamylase.

Alternatively, yeast can be transformed with a glucoamylase gene. However, despite the use of yeast expressing a glucoamylase, it is recommended to always require additional glucoamylase to yield maximum yield, and as a consequence glucoamylase is always added.

For example, Petit et al, in their poster abstract titled "Engineering industrial *Saccharomyces cerevisiae* strains for ethanol production from starchy substrates and byproducts", presented 27-29 Jun. 2017, at the University College Cork in Ireland mention that glucoamylase genes were cloned into the genome of a well-known industrial yeast strain, Ethanol Red. It mentioned that substitution of conventional yeasts with "AMG yeast" reduced the amount of exogenous glucoamylase required for efficient fermentation by around 30-40%. From this it can, however, be deduced that still 60-70% of the original exogenous glucoamylase remained required.

SUMMARY OF THE INVENTION

The invention now provides a process for the production of ethanol comprising:
fermenting an, optionally liquefied, corn slurry under anaerobic conditions in the presence of a recombinant yeast; and
recovering the ethanol,
wherein said recombinant yeast functionally expresses a heterologous nucleic acid sequence encoding a glucoamylase (GA) having an amino acid sequence according to SEQ ID NO: 1 or which glucoamylase is a functional homologue thereof having a sequence identity of at least 80%, or which glucoamylase is a functional homologue which is derived, by way of one or more amino acid substitutions, deletions or insertions, from the amino acid sequence of SEQ ID NO: 1; and wherein the process comprises dosing a glucoamylase at a concentration of 0.05 g/L or less, expressed as the total amount of glucoamylase enzyme in grams per liter of corn slurry.

The corn slurry is optionally liquefied and preferably the fermenting comprises the fermenting of a liquefied corn slurry under anaerobic conditions in the presence of the recombinant yeast.

Preferably the recombinant yeast functionally expresses a heterologous nucleic acid sequence encoding a glucoamylase (GA) having an amino acid sequence according to SEQ ID NO: 1 or which glucoamylase is a functional homologue thereof having a sequence identity of preferably at least 85%, at least 90%, at least 95%, at least 98% or at least 99%, or which glucoamylase is a functional homologue which is derived, by way of one or more amino acid substitutions, deletions or insertions, from the amino acid sequence of SEQ ID NO: 1.

The process according to the invention has both operational as well as economic advantages. The inventors have found that using a yeast functionally expressing a glucoamylase having an amino acid sequence according to SEQ ID NO: 1 or a functional homologue thereof advantageously requires little or even no dosing of glucoamylase.

BRIEF DESCRIPTION OF THE SEQUENCE LISTINGS

TABLE 1

Short description of the sequences

| SEQ ID NO | Description |
|---|---|
| 1 | *Punctularia strigosozonata* glucoamylase (mature) |
| 2 | *Punctularia strigosozonata* glucoamylase (mature) with native signal sequence |
| 3 | *Punctularia strigosozonata* glucoamylase signal sequence |
| 4 | connector sequence |
| 5 | connector sequence |
| 6 | integration target sequence |
| 7 | integration target sequence |

DETAILED DESCRIPTION OF A PREFERRED EMBODIMENT

The term "a" or "an" as used herein is defined as "at least one" unless specified otherwise.

When referring to a noun (e.g. a compound, an additive, etc.) in the singular, the plural is meant to be included. Thus, when referring to a specific moiety, e.g. "gene" or "nucleotide sequence", this means "at least one" of that gene or nucleotide sequence, e.g. "at least one gene" or "at least one nucleotide sequence" unless specified otherwise. The term 'or' as used herein is to be understood as 'and/or'.

When referring to a compound of which several isomers exist (e.g. a D and an L enantiomer), the compound in principle includes all enantiomers, diastereomers and cis/ trans isomers of that compound that may be used in the particular method of the invention; in particular when referring to such as compound, it includes the natural isomer(s).

The term 'fermentation', 'fermentative' and the like is used herein in a classical sense, i.e. to indicate that a process is or has been carried out under anaerobic conditions. Anaerobic conditions are herein defined as conditions without any oxygen or in which essentially no oxygen is consumed by the cell, in particular a yeast cell, and usually corresponds to an oxygen consumption of less than 5 mmol/l·h$^{-1}$, in particular to an oxygen consumption of less than 2.5 mmol/l·h$^{-1}$, or less than 1 mmol/l·h$^{-1}$. More preferably 0 mmol/L/h is consumed (i.e. oxygen consumption is not detectable. This usually corresponds to a dissolved oxygen concentration in the culture broth of less than 5% of air saturation, in particular to a dissolved oxygen concentration of less than 1% of air saturation, or less than 0.2% of air saturation.

The term "yeast" or "yeast cell" refers to a phylogenetically diverse group of single-celled fungi, most of which are in the division of Ascomycota and Basidiomycota. The budding yeasts ("true yeasts") are classified in the order Saccharomycetales, with *Saccharomyces cerevisiae* as the most well-known species.

The term "recombinant yeast" as used herein, refers to a yeast strain containing nucleic acid which is the result of one or more genetic modifications using recombinant DNA technique(s) and/or another mutagenic technique(s). In particular a recombinant yeast may comprise nucleic acid not present in a corresponding wild-type cell, which nucleic acid has been introduced into that strain (cell) using recombinant DNA techniques (a transgenic cell), or which nucleic acid not present in said wild-type is the result of one or more mutations—for example using recombinant DNA techniques or another mutagenesis technique such as UV-irradiation—in a nucleic acid sequence present in said wild-type (such as a gene encoding a wild-type polypeptide) or wherein the nucleic acid sequence of a gene has been modified to target the polypeptide product (encoding it) towards another cellular compartment. Further, the term "recombinant" in particular relates to a strain (cell) from which DNA sequences have been removed using recombinant DNA techniques.

The term "transgenic (yeast) cell" as used herein, refers to a strain (cell) containing nucleic acid not naturally occurring in that strain (cell) and which has been introduced into that strain (cell) using recombinant DNA techniques, i.e. a recombinant cell).

The term "mutated" as used herein regarding proteins or polypeptides means that at least one amino acid in the wild-type or naturally occurring protein or polypeptide sequence has been replaced with a different amino acid, inserted or deleted from the sequence via mutagenesis of nucleic acids encoding these amino acids. Mutagenesis is a well-known method in the art, and includes, for example, site-directed mutagenesis by means of PCR or via oligo-nucleotide-mediated mutagenesis as described in Sambrook et al., Molecular Cloning—A Laboratory Manual, 2nd ed., Vol. 1-3 (1989). The term "mutated" as used herein regarding genes means that at least one nucleotide in the nucleic acid sequence of that gene or a regulatory sequence thereof, has been replaced with a different nucleotide, or has been deleted from the sequence via mutagenesis, resulting in the transcription of a protein sequence with a qualitatively or quantitatively altered function or the knock-out of that gene.

In the context of this invention an "altered gene" has the same meaning as a mutated gene.

The term "gene", as used herein, refers to a nucleic acid sequence containing a template for a nucleic acid polymerase, in eukaryotes, RNA polymerase II. Genes are transcribed into mRNAs that are then translated into protein.

The term "nucleic acid" as used herein, includes reference to a deoxyribonucleotide or ribonucleotide polymer, i.e. a polynucleotide, in either single or double-stranded form, and unless otherwise limited, encompasses known analogues having the essential nature of natural nucleotides in that they hybridize to single-stranded nucleic acids in a manner similar to naturally occurring nucleotides (e. g., peptide nucleic acids). A polynucleotide can be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including among other things, simple and complex cells.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The essential nature of such analogues of naturally occurring amino acids is that, when incorporated into a protein, that protein is specifically reactive to antibodies elicited to the same protein but consisting entirely of naturally occurring amino acids. The terms "polypeptide", "peptide" and "protein" are also inclusive of modifications including, but not limited to, glycosylation, lipid attachment, sulphation, gamma-carboxylation of glutamic acid residues, hydroxylation and ADP-ribosylation.

When an enzyme is mentioned with reference to an enzyme class (EC), the enzyme class is a class wherein the enzyme is classified or may be classified, on the basis of the Enzyme Nomenclature provided by the Nomenclature Committee of the International Union of Biochemistry and Molecular Biology (NC-IUBMB), which nomenclature may be found at http://www.chem.qmul.ac.uk/iubmb/enzyme/. Other suitable enzymes that have not (yet) been classified in a specified class but may be classified as such, are meant to be included.

If referred herein to a protein or a nucleic acid sequence, such as a gene, by reference to a accession number, this number in particular is used to refer to a protein or nucleic acid sequence (gene) having a sequence as can be found via www.ncbi.nlm.nih.gov/, (as available on 14 Jun. 2016) unless specified otherwise.

Every nucleic acid sequence herein that encodes a polypeptide also, by reference to the genetic code, describes every possible silent variation of the nucleic acid. The term "conservatively modified variants" applies to both amino acid and nucleic acid sequences. With respect to particular nucleic acid sequences, conservatively modified variants refers to those nucleic acids which encode identical or conservatively modified variants of the amino acid sequences due to the degeneracy of the genetic code. The term "degeneracy of the genetic code" refers to the fact that a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations" and represent one species of conservatively modified variation.

The term "functional homologue" (or in short "homologue") of a polypeptide having a specific sequence (e.g. "SEQ ID NO: X"), as used herein, refers to a polypeptide comprising said specific sequence with the proviso that one or more amino acids are substituted, deleted, added, and/or inserted, and which polypeptide has (qualitatively) the same enzymatic functionality for substrate conversion. This functionality may be tested by use of an assay system comprising a recombinant cell comprising an expression vector for the expression of the homologue in yeast, said expression vector comprising a heterologous nucleic acid sequence operably linked to a promoter functional in the yeast and said heterologous nucleic acid sequence encoding the homologous polypeptide of which enzymatic activity for converting acetyl-Coenzyme A to acetaldehyde in the cell is to be tested, and assessing whether said conversion occurs in said cells. Candidate homologues may be identified by using in silico similarity analyses. A detailed example of such an analysis is described in Example 2 of WO2009/013159. The skilled person will be able to derive there from how suitable candidate homologues may be found and, optionally upon codon(pair) optimization, will be able to test the required functionality of such candidate homologues using a suitable assay system as described above. A suitable homologue represents a polypeptide having an amino acid sequence similar to a specific polypeptide of more than 50%, preferably of 60% or more, in particular of at least 70%, more in particular of at least 80%, at least 90%, at least 95%, at least 97%, at least 98% or at least 99% and having the required enzymatic functionality. With respect to nucleic acid sequences, the term functional homologue is meant to include nucleic acid sequences which differ from another nucleic acid sequence due to the degeneracy of the genetic code and encode the same polypeptide sequence.

Sequence identity is herein defined as a relationship between two or more amino acid (polypeptide or protein) sequences or two or more nucleic acid (polynucleotide) sequences, as determined by comparing the sequences. Usually, sequence identities or similarities are compared over the whole length of the sequences compared. In the art, "identity" also means the degree of sequence relatedness between amino acid or nucleic acid sequences, as the case may be, as determined by the match between strings of such sequences.

Amino acid or nucleotide sequences are said to be homologous when exhibiting a certain level of similarity. Two sequences being homologous indicate a common evolutionary origin. Whether two homologous sequences are closely related or more distantly related is indicated by "percent identity" or "percent similarity", which is high or low respectively. Although disputed, to indicate "percent identity" or "percent similarity", "level of homology" or "percent homology" are frequently used interchangeably. A comparison of sequences and determination of percent identity between two sequences can be accomplished using a mathematical algorithm. The skilled person will be aware of the fact that several different computer programs are available to align two sequences and determine the homology between two sequences (Kruskal, J. B. (1983) An overview of sequence comparison In D. Sankoff and J. B. Kruskal, (ed.), Time warps, string edits and macromolecules: the theory and practice of sequence comparison, pp. 1-44 Addison Wesley). The percent identity between two amino acid sequences can be determined using the Needleman and Wunsch algorithm for the alignment of two sequences. (Needleman, S. B. and Wunsch, C. D. (1970) J. Mol. Biol. 48, 443-453). The algorithm aligns amino acid sequences as well as nucleotide sequences. The Needleman-Wunsch algorithm has been implemented in the computer program NEEDLE. For the purpose of this invention the NEEDLE program from the EMBOSS package was used (version 2.8.0 or higher, EMBOSS: The European Molecular Biology Open Software Suite (2000) Rice, P. Longden, I. and Bleasby, A. Trends in Genetics 16, (6) pp 276-277, http://emboss.bioinformatics.nl/). For protein sequences, EBLOSUM62 is used for the substitution matrix. For nucleotide sequences, EDNAFULL is used. Other matrices can be specified. The optional parameters used for alignment of amino acid sequences are a gap-open penalty of 10 and a gap extension penalty of 0.5. The skilled person will appreciate that all these different parameters will yield slightly different results but that the overall percentage identity of two sequences is not significantly altered when using different algorithms.

The homology or identity is the percentage of identical matches between the two full sequences over the total aligned region including any gaps or extensions. The homology or identity between the two aligned sequences is calculated as follows: Number of corresponding positions in the alignment showing an identical amino acid in both sequences divided by the total length of the alignment including the gaps. The identity defined as herein can be obtained from NEEDLE and is labelled in the output of the program as "IDENTITY".

The homology or identity between the two aligned sequences is calculated as follows: Number of corresponding positions in the alignment showing an identical amino acid in both sequences divided by the total length of the alignment after subtraction of the total number of gaps in the alignment. The identity defined as herein can be obtained from NEEDLE by using the NOBRIEF option and is labelled in the output of the program as "longest-identity".

A variant of a nucleotide or amino acid sequence disclosed herein may also be defined as a nucleotide or amino acid sequence having one or several substitutions, insertions and/or deletions as compared to the nucleotide or amino acid sequence specifically disclosed herein (e.g. in de the sequence listing).

Nucleotide sequences of the invention may also be defined by their capability to hybridise with parts of specific nucleotide sequences disclosed herein, respectively, under moderate, or preferably under stringent hybridisation conditions. Stringent hybridisation conditions are herein defined as conditions that allow a nucleic acid sequence of at least about 25, preferably about 50 nucleotides, 75 or 100 and most preferably of about 200 or more nucleotides, to hybridise at a temperature of about 65° C. in a solution comprising about 1 M salt, preferably 6×SSC or any other solution having a comparable ionic strength, and washing at 65° C. in a solution comprising about 0.1 M salt, or less, preferably 0.2×SSC or any other solution having a comparable ionic strength. Preferably, the hybridisation is performed overnight, i.e. at least for 10 hours and preferably washing is performed for at least one hour with at least two changes of the washing solution. These conditions will usually allow the specific hybridisation of sequences having about 90% or more sequence identity.

Moderate conditions are herein defined as conditions that allow a nucleic acid sequences of at least 50 nucleotides, preferably of about 200 or more nucleotides, to hybridise at a temperature of about 45° C. in a solution comprising about 1 M salt, preferably 6×SSC or any other solution having a comparable ionic strength, and washing at room temperature in a solution comprising about 1 M salt, preferably 6×SSC or any other solution having a comparable ionic strength. Preferably, the hybridisation is performed overnight, i.e. at least for 10 hours, and preferably washing is performed for at least one hour with at least two changes of the washing solution. These conditions will usually allow the specific hybridisation of sequences having up to 50% sequence identity. The person skilled in the art will be able to modify these hybridisation conditions in order to specifically identify sequences varying in identity between 50% and 90%.

"Expression" refers to the transcription of a gene into structural RNA (rRNA, tRNA) or messenger RNA (mRNA) with subsequent translation into a protein.

As used herein, "heterologous" in reference to a nucleic acid or protein is a nucleic acid or protein that originates from a foreign species, or, if from the same species, is substantially modified from its native form in composition and/or genomic locus by deliberate human intervention. For example, a promoter operably linked to a heterologous structural gene is from a species different from that from which the structural gene was derived, or, if from the same species, one or both are substantially modified from their original form. A heterologous protein may originate from a foreign species or, if from the same species, is substantially modified from its original form by deliberate human intervention.

The term "heterologous expression" refers to the expression of heterologous nucleic acids in a host cell. The expression of heterologous proteins in eukaryotic host cell systems such as yeast are well known to those of skill in the art. A polynucleotide comprising a nucleic acid sequence of a gene encoding an enzyme with a specific activity can be expressed in such a eukaryotic system. In some embodiments, transformed/transfected cells may be employed as expression systems for the expression of the enzymes. Expression of heterologous proteins in yeast is well known. Sherman, F., et al., Methods in Yeast Genetics, Cold Spring Harbor Laboratory (1982) is a well-recognized work describing the various methods available to express proteins in yeast. Two widely utilized yeasts are *Saccharomyces cerevisiae* and *Pichia pastoris*. Vectors, strains, and protocols for expression in *Saccharomyces* and *Pichia* are known in the art and available from commercial suppliers (e.g., Invitrogen). Suitable vectors usually have expression control sequences, such as promoters, including 3-phosphoglycerate kinase or alcohol oxidase, and an origin of replication, termination sequences and the like as desired.

As used herein "promoter" is a DNA sequence that directs the transcription of a (structural) gene. Typically, a promoter is located in the 5'-region of a gene, proximal to the transcriptional start site of a (structural) gene. Promoter sequences may be constitutive, inducible or repressible. In an embodiment there is no (external) inducer needed.

The term "vector" as used herein, includes reference to an autosomal expression vector and to an integration vector used for integration into the chromosome.

The term "expression vector" refers to a DNA molecule, linear or circular, that comprises a segment encoding a polypeptide of interest under the control of (i.e. operably linked to) additional nucleic acid segments that provide for its transcription. Such additional segments may include promoter and terminator sequences, and may optionally include one or more origins of replication, one or more selectable markers, an enhancer, a polyadenylation signal, and the like. Expression vectors are generally derived from plasmid or viral DNA, or may contain elements of both. In particular an expression vector comprises a nucleic acid sequence that comprises in the 5' to 3' direction and operably linked: (a) a yeast-recognized transcription and translation initiation region, (b) a coding sequence for a polypeptide of interest, and (c) a yeast-recognized transcription and translation termination region. "Plasmid" refers to autonomously replicating extrachromosomal DNA which is not integrated into a microorganism's genome and is usually circular in nature.

An "integration vector" refers to a DNA molecule, linear or circular, that can be incorporated in a microorganism's genome and provides for stable inheritance of a gene encoding a polypeptide of interest. The integration vector generally comprises one or more segments comprising a gene sequence encoding a polypeptide of interest under the control of (i.e. operably linked to) additional nucleic acid segments that provide for its transcription. Such additional segments may include promoter and terminator sequences, and one or more segments that drive the incorporation of the gene of interest into the genome of the target cell, usually by the process of homologous recombination. Typically, the integration vector will be one which can be transferred into the target cell, but which has a replicon which is nonfunctional in that organism. Integration of the segment comprising the gene of interest may be selected if an appropriate marker is included within that segment.

By "host cell" is meant a cell which contains a vector and supports the replication and/or expression of the vector.

"Transformation" and "transforming", as used herein, refers to the insertion of an exogenous polynucleotide into a host cell, irrespective of the method used for the insertion, for example, direct uptake, transduction, f-mating or electroporation. The exogenous polynucleotide may be maintained as a non-integrated vector, for example, a plasmid, or alternatively, may be integrated into the host cell genome.

By "disruption" is meant (or includes) all nucleic acid modifications such as nucleotide deletions or substitutions, gene knock-outs, (other) which affect the translation or transcription of the corresponding polypeptide and/or which affect the enzymatic (specific) activity, its substrate specificity, and/or or stability. Such modifications may be targeted on the coding sequence or on the promotor of the gene.

The invention provides a process for the production of ethanol comprising:

fermenting an, optionally liquefied, corn slurry under anaerobic conditions in the presence of a recombinant yeast; and recovering the ethanol, wherein said recombinant yeast functionally expresses a heterologous nucleic acid sequence encoding a glucoamylase (GA) having an amino acid sequence according to SEQ ID NO: 1 or which glucoamylase is a functional homologue thereof having a sequence identity of at least 80%, preferably at least 85%, at least 90%, at least 95%, at least 98%, at least 99%, or which glucoamylase is a functional homologue which is derived, by way of one or more amino acid substitutions, deletions or insertions, from the amino acid sequence of SEQ ID NO: 1, and wherein the process comprises dosing a glucoamylase at a concentration of 0.05 g/L or less, expressed as the total amount of GA enzyme in grams per liter of corn slurry.

The term "dosing" is understood to mean adding GA other than, or in addition to any GA which may be added via the yeast functionally expressing glucoamylase.

The amount of GA can be determined for example by proteomics, or by Western Blot. These techniques are known in the art.

In an embodiment glucoamylase is dosed at a concentration between 0.005 and 0.05 g/L (gram per liter), between 0.01 and 0.05 g/L, between 0.02 and 0.05 g/L, between 0.03 and 0.05 g/L, or between 0.04 and 0.05 g/L. In an embodiment glucoamylase is dosed at concentration between 0.005 and 0.04 g/L, between 0.01 and 0.04 g/L, between 0.02 and 0.04 g/L, or between 0.03 and 0.04 g/L. In an embodiment glucoamylase is dosed at concentration between 0.005 and 0.04 g/L, between 0.005 and 0.03 g/L, between 0.005 and 0.02 g/L, or between 0.005 and 0.01 g/L.

For example, glucoamylase, preferably as a liquid product, may be dosed in an amount equal to or less than 0.05 grams per one kilo corn slurry, preferably in an amount equal to or less than 0.005 grams per one kilo corn slurry.

In an embodiment the process of the invention is carried out without adding any glucoamylase. Hence, the dosage of glucoamylase may even be zero.

The skilled person knows how to dose GA. GA may be dosed to the fermentation. GA can be dosed separately, before or after adding yeast. GA can be dosed as a dry product, e.g. as powder or a granulate, or as a liquid. GA can be dosed together with other components such as antibiotics. GA can also be dosed as part of the back set, i.e. a stream in which part of the thin stillage is recycled e.g. to the fermentation. GA can also be dosed using a combination of these methods.

Glucoamylase (EC 3.2.1.20 or 3.2.1.3), abbreviated herein as GA, and also referred to as amyloglucosidase, alpha-glucosidase, glucan 1,4-alpha glucosidase, maltase glucoamylase, and maltase-glucoamylase, catalyses at least the hydrolysis of terminal 1,4-linked alpha-D-glucose residues from non-reducing ends of amylose chains to release free D-glucose.

The polypeptide of SEQ ID NO: 2 encodes a "mature glucoamylase", referring to the enzyme in its final form after translation and any post-translational modifications, such as N-terminal processing, C-terminal truncation, glycosylation, phosphorylation, etc.

In an embodiment the GA is a variant of the GA having an amino acid sequence according to SEQ ID NO: 2 having a sequence identity of at least 50%, preferably at least 60%, 70%, 75%, 80%, 85%, 90%, 95, 98%, or 99%. Amino acids 1-17 of the SEQ ID NO: 2 may encode for a signal sequence.

A signal sequence (also referred to as signal peptide, targeting signal, localization signal, localization sequence, transit peptide, leader sequence or leader peptide) can be present at the N-terminus of a polypeptide (here, the GA) where it signals that the polypeptide is to be excreted, for example outside the cell and into the media.

The inventors have found that using a yeast functionally expressing a GA having an amino acid sequence according to SEQ ID NO: 1 or a functional homologue thereof advantageously requires little or even no addition of GA.

The recombinant yeast may be subjected to evolutionary engineering to improve its properties. Evolutionary engineering processes are known processes. Evolutionary engineering is a process wherein industrially relevant phenotypes of a microorganism, herein the recombinant yeast, can be coupled to the specific growth rate and/or the affinity for a nutrient, by a process of rationally set-up natural selection. Evolutionary Engineering is for instance described in detail in Kuijper, M, et al, FEMS, Eukaryotic cell Research 5(2005) 925-934, WO2008041840 and WO2009112472. After the evolutionary engineering the resulting pentose fermenting recombinant cell is isolated. The isolation may be executed in any known manner, e.g. by separation of cells from a recombinant cell broth used in the evolutionary engineering, for instance by taking a cell sample or by filtration or centrifugation.

In an embodiment, the recombinant yeast is marker-free. As used herein, the term "marker" refers to a gene encoding a trait or a phenotype which permits the selection of, or the screening for, a host cell containing the marker. Marker-free means that markers are essentially absent in the recombinant yeast. Being marker-free is particularly advantageous when antibiotic markers have been used in construction of the recombinant yeast and are removed thereafter. Removal of markers may be done using any suitable prior art technique, e.g. intramolecular recombination.

In one embodiment, the recombinant yeast is constructed on the basis of an inhibitor tolerant host cell, wherein the construction is conducted as described hereinafter. Inhibitor tolerant host cells may be selected by screening strains for growth on inhibitors containing materials, such as illustrated in Kadar et al, Appl. Biochem. Biotechnol. (2007), Vol. 136-140, 847-858, wherein an inhibitor tolerant *S. cerevisiae* strain ATCC 26602 was selected.

The corn slurry can be combined with another fermentable carbohydrate composition, such as a lignocellulosic hydrolysate, for example corn fiber hydrolysate and/or corn stover hydrolysate. Such other fermentable carbohydrate composition may for example be added in an amount in the range from 0.1% w/w (weight basis) to 45.0% w/w, suitably in the range from 1.0% w/w to 20.0% w/w, based on the total weight of corn slurry. It is also possible for the corn slurry to be added in an amount in the range from 0.1% w/w (weight basis) to 45.0% w/w, suitably in the range from 1.0% w/w to 20.0% w/w to another fermentable carbohydrate composition, such as a lignocellulosic hydrolysate, where the weight percentages are based on the total weight of the other fermentable carbohydrate composition. In 1G practice, however, the presence of another fermentable carbohydrate composition, especially the presence of any lignocellulosic hydrolysate, is preferably limited to equal to or less than 1.0% w/w, more preferably equal to or less than 0.1% w/w, based on the total weight of corn slurry. Most preferably the fermentation is carried out in the essential absence of another fermentable carbohydrate composition, that is, in the essential absence of any lignocellulosic hydrolysate and only corn slurry is used.

In an embodiment one such composition is a biomass hydrolysate. Such biomass hydrolysate may be a lignocellulosic biomass hydrolysate. Lignocellulose herein includes hemicellulose and hemicellulose parts of biomass. Also lignocellulose includes lignocellulosic fractions of biomass. Suitable lignocellulosic materials may be found in the following list: orchard primings, chaparral, mill waste, urban wood waste, municipal waste, logging waste, forest thinnings, short-rotation woody crops, industrial waste, wheat straw, oat straw, rice straw, barley straw, rye straw, flax straw, soy hulls, rice hulls, rice straw, corn gluten feed, oat hulls, sugar cane, corn stover, corn stalks, corn cobs, corn husks, switch grass, miscanthus, sweet sorghum, canola stems, soybean stems, prairie grass, gamagrass, foxtail; sugar beet pulp, citrus fruit pulp, seed hulls, cellulosic animal wastes, lawn clippings, cotton, seaweed, trees, softwood, hardwood, poplar, pine, shrubs, grasses, wheat, wheat straw, sugar cane bagasse, corn, corn husks, corn hobs, corn kernel, fiber from kernels, products and by-products from wet or dry milling of grains, municipal solid waste, waste paper, yard waste, herbaceous material, agricultural residues, forestry residues, municipal solid waste, waste paper, pulp, paper mill residues, branches, bushes, canes, corn, corn husks, an energy crop, forest, a fruit, a flower, a grain, a grass, a herbaceous crop, a leaf, bark, a needle, a log, a root, a sapling, a shrub, switch grass, a tree, a vegetable, fruit peel, a vine, sugar beet pulp, wheat midlings, oat hulls, hard or soft wood, organic waste material generated from an agricultural process, forestry wood waste, or a combination of any two or more thereof. Lignocellulose, which may be considered as a potential renewable feedstock, generally comprises the polysaccharides cellulose (glucans) and hemicelluloses (xylans, heteroxylans and xyloglucans). In addition, some hemicellulose may be present as glucomannans, for example in wood-derived feedstocks. The enzymatic hydrolysis of these polysaccharides to soluble sugars, including both monomers and multimers, for example glucose, cellobiose, xylose, arabinose, galactose, fructose, mannose, rhamnose, ribose, galacturonic acid, glucuronic acid and other hexoses and pentoses occurs under the action of different enzymes acting in concert. In addition, pectins and other pectic substances such as arabinans may make up considerably proportion of the dry mass of typically cell walls from non-woody plant tissues (about a quarter to half of dry mass may be pectins). Lignocellulosic material may be pretreated. The pretreatment may comprise exposing the lignocellulosic material to an acid, a base, a solvent, heat, a peroxide, ozone, mechanical shredding, grinding, milling or rapid depressurization, or a combination of any two or more thereof. This chemical pretreatment is often combined with heat-pretreatment, e.g. between 150-220° C. for 1 to 30 minutes.

In another embodiment such composition is a pre-treated corn stover hydrolysate. Another preferred composition is a corn fiber hydrolysate, which is optionally pre-treated.

In yet another embodiment such composition is a starch hydrolysate, such as a corn starch hydrolysate.

In the context of the invention a "hydrolysate" refers to a polysaccharide that has been depolymerized through the addition of water to form mono and oligosaccharide sugars. Hydrolysates may be produced by enzymatic or acid hydrolysis of the polysaccharide-containing material.

In an embodiment the fermentable carbohydrate is obtained from starch, lignocellulose, and/or pectin.

The starch, lignocellulose, and/or pectin may be contacted with an enzyme composition, wherein one or more sugar is produced, and wherein the produced sugar is fermented to give a fermentation product, wherein the fermentation is conducted with a recombinant yeast of the invention.

The yeast may be selected from Saccharomycetaceae, in particular from the group of *Saccharomyces*, such as *Saccharomyces cerevisiae*; *Kluyveromyces*, such as *Kluyveromyces marxianus*; *Pichia*, such as *Pichia stipitis* or *Pichia angusta*; *Zygosaccharomyces*, such as *Zygosaccharomyces bailii*; and *Brettanomyces*, such as *Brettanomyces intermedius, Issatchenkia*, such as *Issatchenkia orientalis* and *Hansenula*.

In an embodiment the process further comprises the production of dried distillers grains with solubles (DDGS). Such process may comprise:
(a) subjecting corn grain to a milling step and subsequently adding water to yield a corn slurry;
(b) optionally subjecting said corn slurry to a liquefaction step comprising adding amylase and subjecting the corn slurry to a heating step to yield a liquified corn slurry;
(c) fermenting the (optionally liquefied) corn slurry in the presence of a recombinant yeast to yield a fermented mash comprising at least ethanol;
(d) subjecting said fermented grain mash to a distillation step to yield a distillate comprising ethanol and a distillation residue ("whole stillage"), and recovering said whole stillage;
(e) subjecting the whole stillage to a solid-liquid separation step, such as a centrifugation step, to yield a solid fraction ("wet distiller's grains" or "WDG") and a liquid fraction ("thin stillage") and recovering both of the thin stillage and the WDG;
(f) optionally extracting oil from said thin stillage;
(g) concentrating the thin stillage (e.g. by condensation or evaporation) to yield a concentrated fraction ("condensed distillers solubles" or "CDS") and recovering said CDS;
(h) combining at least part of the WDG with at least part of the CDS;
(i) drying the combined WDG and CDS, e.g. by a rotary drier, to produce distillers dried grains with solubles (DDGS);
(j) recycling at least part of the thin stillage the corn starch slurry; and
(k) recovering the ethanol.

In step (a) the whole corn grain (corn kernels) can be ground, typically by using a hammer mill. This results in a flour, or meal. Water and thin stillage are added to the meal, resulting in a slurry. Enzyme (such as amylase) may be added in this step.

The corn slurry may suitably be obtained after slurrying ground and/or milled corn with water and/or thin stillage. By adding water and/or thin stillage a slurry can be obtained. It is, however, also possible to slurry the ground and/or milled corn with other process water, for example condensate water from stillage evaporators and/or bottoms of a rectifier. Any water from a distillation unit can advantageously be used for slurrying the ground and/or milled corn. The corn slurry may be composed of only the ground and/or milled corn and the water and/or thin stillage; or the corn starch in the ground and/or milled corn may optionally be, optionally partly, hydrolysed by an enzyme (such as amylase) into a corn starch hydrolysate. This is generally referred to as a "1G" process. It is also possible to further combine such corn slurry, comprising these so-called 1G components, with corn fiber hydrolysate. This is generally referred to as a "1.5G" process. Also, it is possible to further combine the corn slurry, comprising these so-called 1G components, with lignocellulosic hydrolysates other than corn fiber hydrolysate, such as for example corn stover hydrolysate and/or grain sorghum hydrolysate (also called "milo"). This is generally referred to as a "2G" process.

Optionally, in step (b) enzymes such as amylases are added to the slurry to convert starch to smaller glucose polymers. If in step (a) enzyme is added, more enzyme may be added in step (b). Such enzymes are preferably thermostable. Ammonia is usually added to control the pH and also acts as a nutrient. Next, the slurry is subjected to high temperature, for instance around 80° C. This will kill bacteria and helps liquefaction process by gelatinizing of the starch. The liquefied slurry is usually referred to as "mash" or "corn mash".

Fermentation step (c) typically takes 40 to 50 hours. It is, however, also possible for the fermentation step to take longer, for example to take up to 60 or even up to 65 hours. It is conducted under anaerobic or micro-aerobic conditions. An anaerobic fermentation process is herein defined as a fermentation process run in the absence of oxygen or in which substantially no oxygen is consumed, preferably less than about 5, about 2.5 or about 1 mmol/L/h, more preferably 0 mmol/L/h is consumed (i.e. oxygen consumption is not detectable), and wherein organic molecules serve as both electron donor and electron acceptors. In the absence of oxygen, NADH produced in and biomass formation, cannot be oxidised by oxidative phosphorylation. To solve this problem many microorganisms use pyruvate or one of its derivatives as an electron and hydrogen acceptor thereby regenerating $NAD^+$. The fermentation process is preferably run at a temperature that is optimal for the yeast. Thus, the fermentation process is performed at a temperature which is less than about 50° C., less than about 42° C., or less than about 38° C., preferably at a temperature which is lower than about 35° C., about 33° C., about 30 or about 28° C. and at a temperature which is higher than about 20° C., about 22° C., or about 25° C.

The yeast which is used in the fermentation is typically prepared in a propagation step, in order to multiply the yeast. Such propagation step yeast is carried out aerobically. Propagation step is generally aerated but oxygen limited and can be started by adding dry yeast ("dry pitch"), rehydrated dry yeast, or by adding a cream yeast.

However, it is also possible to exclude a propagation step and start the fermentation by adding (rehydrated) dry yeast ("dry pitch") or by adding cream yeast to the (optionally liquefied) corn starch slurry.

In step (d), the fermented mash (or part of the fermented mash) is either transferred to an intermediate holding vessel ("beerwell") or directly to one or (usually) multiple distillation columns where ethanol is removed, resulting in "whole stillage".

In step (e) the whole stillage (or part of the whole stillage) is subjected to a solid-liquid separation step resulting in a solid fraction, referred to as "wet distillers grains" or WDG, and a liquid fraction ("thin stillage"). The solid-liquid separation is typically done by centrifugation but can also comprise filtration. The thin stillage and the WDG are each recovered.

Optionally oil is extracted from the still stillage to yield crude distillers oil (CDS) according to step (f). Oil is usually extracted from thin stillage using centrifugation. The temperature of the thin stillage is typically increased by heat exchangers using steam to facilitate extraction of the oil. After corn oil extraction, thermal energy from the stillage can be recovered in heat exchangers to heat the incoming stillage. In general, a typical ethanol plant uses corn that contains approximately 4% w/w corn oil (weight basis) which ends up in DDGS if the oil were not extracted.

The thin stillage (or part of the thin stillage) is concentrated to yield condensed distillers solubles (CDS) according to step (g). Part of the thin stillage is recycled to the slurry according to step (j). This is referred to as "back set".

According to step (h) at least part of the WDG is combined with at least part of the CDS.

According to step (i) the combined WDG and CDS are dried to yield dried distillers grains with solubles (DDGS). Typically, for every 3.8 liters of ethanol produced, 2.4 kg of DDGS is produced without the use of corn oil extraction. However, with corn oil extraction, DDGS yield is reduced by approximately 0.06 kg per liter of ethanol produced, representing a 9.4% reduction in DDGS yield.

EXAMPLES

Example 1

This Example relates to the performance of Saccharomyces cerevisiae strains transformed with glucoamylases from eleven different sources:
  Amorphotheca resinae strain DA0M194228
  Corynascus sepedonium ATCC9787
  Aspergillus niger
  Trichoderma reesei
  Botryotinia fuckliana BcDW1
  Auricularia delicate TFB-10046 SS5
  Talaromyces stipitatus ATCC 10500
  Piriformospora indica DSM 11827
  Punctularia strigosozonata HHB-11173 SS5
  Saccharomycopsis fibuligera
  Saccharomyces diastaticus The strains were made using Ethanol Red as starting strain. Ethanol Red is a commercial Saccharomyces cerevisiae strain, available from Lesaffre. A HIS 3 deletion was made in Ethanol Red by deleting the entire ORF.

Each GA was placed behind its native leader as well as the Saccharomyces cerevisiae alpha mating signal (Sc_Mfalfa.sig) as described in Table 1 of co-pending European patent application EP17193915.0. All expression cassettes were ordered as promoter-ORF-terminator cassette at DNA2.0. All signal sequence-mature ORF combinations are downstream of the Sc_PGK1 promoter and upstream of the Sc_ENO1 terminator.

All expression cassettes were amplified with 50 bp-homology to pRS313 (single copy vector with HIS3 marker). The pRS313 plasmid was amplified as well. For DNA amplifications, Phusion High-Fidelity DNA Polymerase (New England Biolabs) was used according to the manufacturer's instructions. DNA amplifications were carried out using 4 ng of template and a Tm of 60° C. Primer concentrations ranged from 0.5 µM for regular primers to 0.05 µM for longer primers (>50 bp). To remove possible contaminants and residual primers, the reactions were purified using the NucleoSpin96 PCR Clean-up Kit. The pRS313 plasmid with the GA expression cassette was assembled in vivo.

Performance of GAs was tested in two stages. Firstly, strains were tested for micro-aerobic growth in microtiter plate. Eight single colonies per transformation were incubated anaerobically for 48 h at 30° C. in wells containing medium as used and described in J. Bacteriol. December 2000 vol. 182 no. 24 7007-7013 containing 240 g/L maltodextrin and 0.05% glucose at pH4.5 and 32° C. Results are in Table 2. From this first screening it was decided to select glucoamylases from Trichoderma reesei, Talaromyces stipitatus, Piriformospora indica, Punctularia strigosozonata, Saccharomycopsis fibuligera, and Saccharomyces diastaticus, since these were the only glucoamylases resulting in sufficient GA expression to facilitate anaerobic growth on a synthetic medium contain starch as sole C-source.

TABLE 2 micro-aerobic growth in microtiter plate

| | Native leader | Mat alpha leader |
|---|---|---|
| *Amorphotheca resinae* strain DAOM194228 | − | − |
| *Corynascus sepedonium* ATCC9787 | − | − |
| *Aspergillus niger* | − | − |
| *Trichoderma reesei* | + | + |
| *Botryotinia fuckeliana* BcDW1 | − | − |
| *Auricularia delicata* TFB-10046 SS5 | − | − |
| *Talaromyces stipitatus* ATCC 10500 | − | + |
| *Piriformospora indica* DSM 11827 | − | + |
| *Punctularia strigosozonata* HHB-11173 SS5 | + | + |
| *Saccharomycopsis fibuligera* | + | + |
| *Saccharomyces diastaticus* | + | + |

Next, colonies from the strains selected in the micro-aerobic MTP test were tested for growth on maltodextrin in a shake flask (SF) experiment under micro-aerobic conditions in Verduyn medium containing 240 g/L Maltodextrin+0.05% glucose+100× diluted Gibco™ Penicillin Streptomycin (10,000 U/mL) at pH4.5 and 30° C. for 72 h. The ability of degradation of maltodextrin was tested by NMR spectrometry by measuring the amount of α1→4 bonds, indicative of the amount of intact (i.e. not-converted) maltodextrin.

For the quantification of residual maltodextrin, 100 µl of the supernatant sample was transferred accurately into a suitable vial. Subsequently 100 µl internal standard solution, containing maleic acid (20 g/l), EDTA (40 g/l), DSS (4,4-dimethyl-4-silapentane-1-sulfonic acid) (0.5 g/L), and sodium hydroxide until pH 6.40, in 020 was added. This mixture was lyophilized and reconstituted in 600 µl $D_2O$.

1D $^1$H NMR spectra of the clear solution were recorded on a Bruker Avance III HD spectrometer, operating at a proton frequency of 400 MHz, equipped with a prodigy probe, using a pulse program without water suppression (ZG), at a temperature of 295 K, with a 90 degree excitation pulse, acquisition time of 2.0 seconds and a relaxation delay of 40 seconds. The number of scans was set at 8, dummy scans were not used.

The analyte concentration [in gram per liter] was calculated based on the following signals (δ relative to DSS): maltodextrin: α-H1 polyglucose signal (m, 5.56-5.25 ppm), calculated as n=1, and a MW of 162 gram/mol. The signal used for the standard: maleic acid peak around 6.4 ppm (S, 2H). Results are in Table 3.

TABLE 3

Maltose degradation, judged by amount of α (1→4) bonds (arbitrary units)

| Glucoamylase | Leader | α (1→4) bonds | Maltose converted |
|---|---|---|---|
| Control (cells without glucoamylase) | — | 194.71 | 0 |
| *T. reesei* | Native | 81.55 | 58% |
| *Punctularia strigosozonata* | Native | 21.25 | 89% |
| *Saccharomycopsis fibuligera* | Native | 49.35 | 75% |
| *S. cerevisiae diastaticus* | Native | 136.95 | 30% |
| *T. reesei* | Sc_Mfalfa.sig | 71.1 | 63% |
| *Taloromyces stipitatus* | Sc_Mfalfa.sig | 144.32 | 26% |
| *Piriformospora indica* | Sc_Mfalfa.sig | 124.23 | 36% |
| *Punctularia strigosozonata* | Sc_Mfalfa.sig | 19.78 | 90% |
| *Saccharomycopsis fibuligera* | Sc_Mfalfa.sig | 34.68 | 82% |
| *S. cerevisiae diastaticus* | Sc_Mfalfa.sig | 120.25 | 38% |

It can be seen that with both native and *S. cerevisiae* alpha mating signal sequence the *Punctularia strigosozonata* GA gave the best performance.

Example 2

Four copies of the *Punctularia strigosozonata* glucoamylase (GA; SEQ ID NO: 1) containing the native leader sequence (SEQ ID NO: 3) were introduced into Ethanol Red, a commercial *Saccharomyces cerevisiae* yeast available from LeSaffre, using CRISPR-CAS9. In front of the open reading frame (ORF), the *S. cerevisiae* PGK1 promoter was placed, behind the ORF, the *S. cerevisiae* ENO1 terminator was placed. Besides the promoter-ORF-terminator sequence, the GA expression cassette contained on the 5' flank the 2.J connector sequence according to SEQ ID NO: 4 and on the 3' flank the 2.K connector sequence according to SEQ ID NO: 5.

To realize the correct targeted integration, flanks varying in length from 360 bp up to 520 bp containing the same connector sequences as the GA expression cassette, were amplified from the Ethanol Red yeast genome. The GA expression cassettes were targeted to integration loci, INT59 (target sequence according to SEQ ID NO: 6) and YPRcTAU3 (target sequence according to SEQ ID NO: 7) where both alleles were targeted, confirmed by diagnostic PCR. To obtain a marker-free strain, the cells were forced to lose their marker containing plasmids by growing several rounds on non-selective media. Finally, the marker-free strain was stored and named FS0209.

Corn mash (30% (w/w) solids) was prepared by mixing 333 g corn flour (Limagrain, Belgium) per kg mash, with 300 ml/kg thin stillage and 367 ml/kg demineralized water. The pH was adjusted to 5.5 with 2M KOH solution. Starch in the mixture was liquefied by adding 0.02 g/kg of a commercial alpha-amylase (Termamyl, Novozymes), and incubated for 4 hours at 80° C. in a rotary shaker. After liquefaction the pH was adjusted to 4.5 with 2M $H_2SO_4$ solution.

Ethanol red and FS0209 were pre-cultured by inoculating 200 ml YepH (20 g/l phytone peptone, 10 g/l yeast extract) supplemented with 2% w/v glucose, from a cryo-vial and incubated for 20 h in a 500 ml shake flask. To determine the inoculation volume of the yeast, the dry cell weight (DCW) content of the culture is determined by filtration and drying via a CEM-SMART microwave. A quantity of the preculture corresponding to the required inoculation size for the propagations were centrifuged (3 min, 4500×g), washed once with sterile demineralized water, centrifuged once more, resuspended in propagation medium and transferred to the propagation flasks.

Propagations were performed in 100 ml Erlenmeyer shake flasks with a foam stopper for 6 h at 32° C., 150 rpm, creating an aerobic environment. The propagation medium was diluted to a 70% solution, checked for pH 4.5 and was supplied with 1.25 g/l urea and antibiotics (neomycin and PenG). For ethanol red 0.088 g/l commercial amyloglucosidase enzyme (Spirizyme Excel, novozymes) was added.

Fermentations were performed in simultaneous saccharification fermentation (SSF) mode, using 500 ml schott bottles filled with 360 ml of corn mash in an AFM set up (Applikon, Schiedam, the Netherlands). The cornmash was used as such, with addition of 1 g/l urea and antibiotics, pH 4.5. Different concentrations of commercial amyloglucosidase enzyme (Spirizyme Excel, Novozymes) were added to the fermentation bottles. The inoculation of the fermenters was done by transferring 10% of the propagation medium to the fermenters, reaching 400 ml of volume. The pH was not controlled during the fermentations, while temperature was controlled at 32° C. Fermentation samples were taken throughout the run and different components were measured by HPLC analysis using a Dionex Ultimate 3000 HPLC system with column oven TCC-3400 and Autosampler WPS-3000 equipped with a guard column (Bio-Rad H cartridge) and an Aminex HPX-87H column (300×7.8 mm; Bio-Rad, Hercules, USA); elution took place at 65° C. with 5 mM $H_2SO_4$ at 0.55 ml/min; the eluate was monitored using a Refractive Index detector RefractoMax 521. $CO_2$ was measured online during the fermentation. Results are shown in Table 4. Good results are obtained even where glucoamylase is dosed at a concentration of 0.05 g/L or less or even where no glucoamylase is dosed.

TABLE 4

| | Ethanol yields | | | |
|---|---|---|---|---|
| Strain | GA dose (g/kg) | 46 h | 53 h | 72 h |
| Ethanol red | 0.16 | 103.4 | 113.4 | 128.7 |
| Ethanol red | 0 | 15.5 | 15.7 | 16.0 |
| FS0209 | 0.08 | 113.8 | 121.9 | 130.4 |
| FS0209 | 0.04 | 122.3 | 125.7 | 136.5 |
| FS0209 | 0.02 | 107.4 | 113.2 | 122.9 |
| FS0209 | 0 | 119.2 | 122.1 | 123.9 |

The invention claimed is:

1. A process for production of ethanol comprising:
   fermenting a corn slurry under anaerobic conditions in the presence of a recombinant yeast; and
   recovering the ethanol,
   wherein said recombinant yeast expresses a heterologous nucleic acid sequence encoding a glucoamylase that has at least 80% sequence identity to the nucleic acid sequence of SEQ ID NO: 1; and wherein the process comprises dosing the fermentation with a glucoamylase at a concentration of 0.05 g/L or less, expressed as the total amount of glucoamylase enzyme in grams per liter of corn slurry.

2. The process according to claim 1, wherein the yeast is selected from the group consisting of Saccharomycetaceae; *Kluyveromyces*; *Pichia*; *Brettanomyces*; and *Issatchenkia*.

3. The process according to claim 2, wherein the yeast is *Saccharomyces cerevisiae*.

4. The process according to claim 1, wherein the corn slurry is liquefied and the fermenting comprises fermenting liquefied corn slurry under anaerobic conditions in the presence of the recombinant yeast.

5. The process according to claim 1, wherein the corn slurry is combined with another fermentable carbohydrate composition.

6. The process according to claim 1, wherein the corn slurry is combined with corn stover hydrolysate and/or corn fiber hydrolysate, and fermented under anaerobic conditions in the presence of the recombinant yeast.

7. The process according to claim 1, wherein starch, lignocellulose, pectin, or any combination thereof is contacted with an enzyme composition, wherein at least one sugar is produced; and wherein the at least one sugar is fermented to give a fermentation product, wherein fermentation is conducted with the recombinant yeast.

8. The process according to claim 1, wherein glucoamylase is dosed at a concentration between 0.005 g/L and 0.05 g/L.

9. The process according to claim 1, wherein the process is carried out without dosing any glucoamylase.

10. The process according to claim 1, wherein the heterologous nucleic acid sequence has at least 85% sequence identity to the nucleic acid sequence of SEQ ID NO: 1.

11. The process according to claim 1, wherein the heterologous nucleic acid sequence has at least 90% sequence identity to the nucleic acid sequence of SEQ ID NO: 1.

12. The process according to claim 1, wherein the heterologous nucleic acid sequence has at least 95% sequence identity to the nucleic acid sequence of SEQ ID NO: 1.

13. The process according to claim 1, wherein the heterologous nucleic acid sequence has at least 98% sequence identity to the nucleic acid sequence of SEQ ID NO: 1.

14. The process according to claim 1, wherein the heterologous nucleic acid sequence has at least 99% sequence identity to the nucleic acid sequence of SEQ ID NO: 1.

15. The process according to claim 1, wherein the heterologous nucleic acid sequence has 100% sequence identity to the nucleic acid sequence of SEQ ID NO: 1.

* * * * *

SEQUENCE LISTING

```
<160> NUMBER OF SEQ ID NOS: 7

<210> SEQ ID NO 1
<211> LENGTH: 561
<212> TYPE: PRT
<213> ORGANISM: Punctularia strigosozonata
<220> FEATURE:
<221> NAME/KEY: MISC_FEATURE
<222> LOCATION: (1)..(561)
<223> OTHER INFORMATION: Punctularia strigosozonata glucoamylase

<400> SEQUENCE: 1

Ser Ser Lys Ser Val Ser Ala Tyr Ile Ser Ser Glu Ser Pro Ile Ala
1               5                   10                  15

His Ser Lys Leu Leu Asp Asn Ile Gly Pro Asp Gly Ala Lys Ala Pro
            20                  25                  30

Gly Ala Phe Pro Gly Val Val Val Ala Ser Pro Ser Thr Asp Asn Pro
        35                  40                  45

Asn Tyr Tyr Tyr Ser Trp Ile Arg Asp Ser Ser Leu Val Phe Lys Thr
    50                  55                  60

Leu Ile Asp Asp Tyr Val Asn Gly Lys Asn Thr Ser Lys Ser Leu Arg
65                  70                  75                  80

Ser Leu Ile Asp Asp Phe Val Thr Ala Ser Ser Val Phe Gln Gln Thr
                85                  90                  95

Pro Asn Pro Ser Gly Asn Val Ser Thr Gly Gly Leu Gly Glu Pro Lys
            100                 105                 110

Phe Tyr Val Asn Glu Thr Ala Phe Leu Asp Ser Trp Gly Arg Pro Gln
        115                 120                 125

Arg Asp Gly Pro Ala Leu Arg Ser Thr Ala Leu Ile Thr Tyr Ala Asn
130                 135                 140

Tyr Leu Leu Asp Asn Asp Asn Thr Thr Trp Val Lys Asp Thr Leu Trp
145                 150                 155                 160

Pro Ile Ile Glu Leu Asp Val Asn Tyr Val Ser Asp Phe Trp Asn Tyr
                165                 170                 175

Thr Thr Phe Asp Leu Trp Glu Glu Val Ala Ser Ser Phe Phe Thr
            180                 185                 190

Thr Ala Val Gln His Arg Ala Leu Arg Gln Ala Ser Lys Leu Ala Lys
        195                 200                 205

Thr Leu Asp Lys Thr Asp Asn Ile Asp Ser Trp Asn Thr Gln Ala Asp
    210                 215                 220

Asn Val Leu Cys Phe Leu Gln Ser Tyr Trp Asn Gly Ser Ala Ile Ile
225                 230                 235                 240

Ala Asn Thr Gly Gly Gly Arg Ser Gly Ile Asp Ala Asn Thr Val Leu
```

```
                    245                 250                 255
Ala Ser Ile His Thr Phe Asp Ser Ser Ala Gly Cys Asp Ala Thr Thr
            260                 265                 270

Phe Gln Pro Cys Ser Asp Lys Ala Leu Ser Asn Leu Lys Val Tyr Val
        275                 280                 285

Asp Ala Phe Arg Ser Ile Tyr Glu Ile Asn Ser Gly Ile Asp Pro Asn
    290                 295                 300

Ala Ala Val Ala Thr Gly Arg Tyr Pro Glu Asp Val Phe Tyr Asp Gly
305                 310                 315                 320

Asn Pro Trp Tyr Leu Ala Thr Ala Val Ala Glu Gln Leu Tyr Asp
                325                 330                 335

Ala Leu Tyr Val Trp Asn Thr Thr Gly Ser Leu Glu Ile Thr Asp Ile
            340                 345                 350

Ser Leu Pro Phe Phe Gln Phe Asp Ser Asp Val Lys Thr Gly Thr
        355                 360                 365

Tyr Ser Asp Asp Asp Thr Phe Asp Ser Leu Ile Ser Ser Ile Gln Ser
    370                 375                 380

Phe Ala Asp Gly Phe Leu Glu Ile His Ala Lys Tyr Thr Pro Asp Asp
385                 390                 395                 400

Gly Ala Leu Ser Glu Glu Phe Ser Lys Thr Asp Gly Ser Gln Thr Ser
                405                 410                 415

Ala Ala Asp Leu Thr Trp Ser Tyr Ala Ala Leu Thr Ala Phe Asp
            420                 425                 430

Ala Arg Ser Arg Asp Ala Ala Val Lys Trp Gly Ala Lys Gly Leu Gln
        435                 440                 445

Val Pro Asp Gly Thr Cys Lys Thr Asn Glu Gly Gly Asp Asp Gly Leu
    450                 455                 460

Gly Val Pro Val Thr Phe Leu Val Lys Asp Ala Glu Thr Val Glu Gly
465                 470                 475                 480

Gln Ser Val Tyr Ile Thr Gly Ser Ile Ala Thr Leu Lys Ser Trp Ser
                485                 490                 495

Pro Asp Asp Ala Leu Leu Met Ser Pro Ser Asp Tyr Pro Thr Trp Thr
            500                 505                 510

Leu Thr Val Asn Leu Ser Ala Ser Glu Ser Val Gln Tyr Lys Tyr Ile
        515                 520                 525

Lys Lys Asp Thr Ala Gly Thr Val Ile Trp Glu Ser Asp Pro Asn Asn
    530                 535                 540

Ser Leu Leu Val Pro Ser Gly Gly Ser Val Thr Thr Asp Asp Thr Trp
545                 550                 555                 560

Arg

<210> SEQ ID NO 2
<211> LENGTH: 578
<212> TYPE: PRT
<213> ORGANISM: Punctularia strigosozonata
<220> FEATURE:
<221> NAME/KEY: MISC_FEATURE
<222> LOCATION: (1)..(578)
<223> OTHER INFORMATION: Punctularia strigosozonata glucoamylase with
      native signal sequence FGA09

<400> SEQUENCE: 2

Met Leu Ser Ser Leu Ile Val Ser Gly Leu Leu Ala Ser Gly Val Cys
1               5                   10                  15

Ala Ser Ser Lys Ser Val Ser Ala Tyr Ile Ser Ser Glu Ser Pro Ile
            20                  25                  30
```

```
Ala His Ser Lys Leu Leu Asp Asn Ile Gly Pro Asp Gly Ala Lys Ala
        35                  40                  45

Pro Gly Ala Phe Pro Gly Val Val Ala Ser Pro Ser Thr Asp Asn
50                  55                  60

Pro Asn Tyr Tyr Tyr Ser Trp Ile Arg Asp Ser Ser Leu Val Phe Lys
65                  70                  75                  80

Thr Leu Ile Asp Asp Tyr Val Asn Gly Lys Asn Thr Ser Lys Ser Leu
                85                  90                  95

Arg Ser Leu Ile Asp Asp Phe Val Thr Ala Ser Ser Val Phe Gln Gln
                100                 105                 110

Thr Pro Asn Pro Ser Gly Asn Val Ser Thr Gly Gly Leu Gly Glu Pro
        115                 120                 125

Lys Phe Tyr Val Asn Glu Thr Ala Phe Leu Asp Ser Trp Gly Arg Pro
        130                 135                 140

Gln Arg Asp Gly Pro Ala Leu Arg Ser Thr Ala Leu Ile Thr Tyr Ala
145                 150                 155                 160

Asn Tyr Leu Leu Asp Asn Asp Asn Thr Thr Trp Val Lys Asp Thr Leu
                165                 170                 175

Trp Pro Ile Ile Glu Leu Asp Val Asn Tyr Val Ser Asp Phe Trp Asn
                180                 185                 190

Tyr Thr Thr Phe Asp Leu Trp Glu Glu Val Ala Ser Ser Phe Phe
        195                 200                 205

Thr Thr Ala Val Gln His Arg Ala Leu Arg Gln Ala Ser Lys Leu Ala
        210                 215                 220

Lys Thr Leu Asp Lys Thr Asp Asn Ile Asp Ser Trp Asn Thr Gln Ala
225                 230                 235                 240

Asp Asn Val Leu Cys Phe Leu Gln Ser Tyr Trp Asn Gly Ser Ala Ile
                245                 250                 255

Ile Ala Asn Thr Gly Gly Gly Arg Ser Gly Ile Asp Ala Asn Thr Val
                260                 265                 270

Leu Ala Ser Ile His Thr Phe Asp Ser Ser Ala Gly Cys Asp Ala Thr
                275                 280                 285

Thr Phe Gln Pro Cys Ser Asp Lys Ala Leu Ser Asn Leu Lys Val Tyr
        290                 295                 300

Val Asp Ala Phe Arg Ser Ile Tyr Glu Ile Asn Ser Gly Ile Asp Pro
305                 310                 315                 320

Asn Ala Ala Val Ala Thr Gly Arg Tyr Pro Glu Asp Val Phe Tyr Asp
                325                 330                 335

Gly Asn Pro Trp Tyr Leu Ala Thr Ala Val Ala Glu Gln Leu Tyr
        340                 345                 350

Asp Ala Leu Tyr Val Trp Asn Thr Thr Gly Ser Leu Glu Ile Thr Asp
        355                 360                 365

Ile Ser Leu Pro Phe Phe Gln Gln Phe Asp Ser Asp Val Lys Thr Gly
        370                 375                 380

Thr Tyr Ser Asp Asp Asp Thr Phe Asp Ser Leu Ile Ser Ser Ile Gln
385                 390                 395                 400

Ser Phe Ala Asp Gly Phe Leu Glu Ile His Ala Lys Tyr Thr Pro Asp
                405                 410                 415

Asp Gly Ala Leu Ser Glu Glu Phe Ser Lys Thr Asp Gly Ser Gln Thr
                420                 425                 430

Ser Ala Ala Asp Leu Thr Trp Ser Tyr Ala Ala Leu Thr Ala Phe
        435                 440                 445
```

```
Asp Ala Arg Ser Arg Asp Ala Ala Val Lys Trp Gly Ala Lys Gly Leu
    450                 455                 460

Gln Val Pro Asp Gly Thr Cys Lys Thr Asn Glu Gly Gly Asp Asp Gly
465                 470                 475                 480

Leu Gly Val Pro Val Thr Phe Leu Val Lys Asp Ala Glu Thr Val Glu
                485                 490                 495

Gly Gln Ser Val Tyr Ile Thr Gly Ser Ile Ala Thr Leu Lys Ser Trp
            500                 505                 510

Ser Pro Asp Asp Ala Leu Leu Met Ser Pro Ser Asp Tyr Pro Thr Trp
        515                 520                 525

Thr Leu Thr Val Asn Leu Ser Ala Ser Glu Ser Val Gln Tyr Lys Tyr
    530                 535                 540

Ile Lys Lys Asp Thr Ala Gly Thr Val Ile Trp Glu Ser Asp Pro Asn
545                 550                 555                 560

Asn Ser Leu Leu Val Pro Ser Gly Gly Ser Val Thr Thr Asp Thr
                565                 570                 575

Trp Arg

<210> SEQ ID NO 3
<211> LENGTH: 17
<212> TYPE: PRT
<213> ORGANISM: Punctularia strigosozonata
<220> FEATURE:
<221> NAME/KEY: MISC_FEATURE
<222> LOCATION: (1)..(17)
<223> OTHER INFORMATION: Punctularia strigosozonata glucoamylase signal
      sequence

<400> SEQUENCE: 3

Met Leu Ser Ser Leu Ile Val Ser Gly Leu Leu Ala Ser Gly Val Cys
1               5                   10                  15

Ala

<210> SEQ ID NO 4
<211> LENGTH: 50
<212> TYPE: DNA
<213> ORGANISM: Artificial Sequence
<220> FEATURE:
<223> OTHER INFORMATION: connector sequence

<400> SEQUENCE: 4
tcctgtacgc actttgtccc acaaattccc gattccgcaa tttgttcgcc            50

<210> SEQ ID NO 5
<211> LENGTH: 50
<212> TYPE: DNA
<213> ORGANISM: Artificial Sequence
<220> FEATURE:
<223> OTHER INFORMATION: connector sequence

<400> SEQUENCE: 5
gaacaggata tttcgatctt ggatacgtac tcgcttgtgt ctggtttcgt            50

<210> SEQ ID NO 6
<211> LENGTH: 20
<212> TYPE: DNA
<213> ORGANISM: Artificial Sequence
<220> FEATURE:
<223> OTHER INFORMATION: integration target sequence

<400> SEQUENCE: 6
agaaaactct tagcttttcc                                             20
```

```
<210> SEQ ID NO 7
<211> LENGTH: 20
<212> TYPE: DNA
<213> ORGANISM: Artificial Sequence
<220> FEATURE:
<223> OTHER INFORMATION: integration target sequence

<400> SEQUENCE: 7
caatatggta tgccgagtct                                               20
```